United States Patent
Zhang et al.

(10) Patent No.: US 12,172,165 B2
(45) Date of Patent: Dec. 24, 2024

(54) REACTION VESSEL, MOLECULAR HYBRIDIZATION APPARATUS, APPLICATION THEREOF, AND DETECTION METHOD

(71) Applicant: LEADWAY (HK) LIMITED, Sheung Wan (CN)

(72) Inventors: Hao Zhang, Zhejiang (CN); Liang Shi, Zhejiang (CN); Yigang Yang, Zhejiang (CN); Yan Zhao, Zhejiang (CN); Zhiheng Wang, Zhejiang (CN); Xiufeng Wang, Zhejiang (CN); Zhihai Wang, Zhejiang (CN); Guochao Miao, Zhejiang (CN); Xiaoheng Xie, Zhejiang (CN)

(73) Assignee: LEADWAY (HK) LIMITED, Sheung Wan (CN)

( * ) Notice: Subject to any disclaimer, the term of this patent is extended or adjusted under 35 U.S.C. 154(b) by 731 days.

(21) Appl. No.: 17/298,906

(22) PCT Filed: Nov. 28, 2019

(86) PCT No.: PCT/CN2019/121746
§ 371 (c)(1),
(2) Date: Jun. 1, 2021

(87) PCT Pub. No.: WO2020/108582
PCT Pub. Date: Jun. 4, 2020

(65) Prior Publication Data
US 2022/0016621 A1 Jan. 20, 2022

(30) Foreign Application Priority Data
Dec. 1, 2018 (CN) .......................... 201811460594.9

(51) Int. Cl.
*B01L 3/00* (2006.01)
*B01L 3/02* (2006.01)
*C12Q 1/6837* (2018.01)

(52) U.S. Cl.
CPC ........... *B01L 3/5082* (2013.01); *B01L 3/0293* (2013.01); *C12Q 1/6837* (2013.01);
(Continued)

(58) Field of Classification Search
CPC ................. B01L 3/5082; B01L 3/0293; B01L 2200/025; B01L 2200/16; B01L 2300/0825; C12Q 1/6837
See application file for complete search history.

(56) References Cited

U.S. PATENT DOCUMENTS

| 6,020,187 A | 2/2000 | Tam |
| 2007/0178606 A1 | 8/2007 | Imoarai et al. |
| 2009/0038416 A1 | 2/2009 | Bonner |

FOREIGN PATENT DOCUMENTS

| CN | 2603936 Y | 2/2004 |
| CN | 201740781 U | 2/2011 |

(Continued)

OTHER PUBLICATIONS

International Search Report issued in PCT/CN2019/121746 dated Jan. 23, 2020—incl Engl lang transl.

(Continued)

*Primary Examiner* — Jill A Warden
*Assistant Examiner* — Michael Stanley Gzybowski
(74) *Attorney, Agent, or Firm* — Michael A. Whittaker

(57) ABSTRACT

Provided is a reaction cup, comprising cup walls and a cup bottom. The cup walls are provided with clamping portions, the clamping portions can allow a membrane strip to stand upright in the reaction cup, and the connecting area of the two opposite clamping portions forms an upright placement (Continued)

position for the membrane strip. The present invention further provides a molecular hybridization instrument used with the reaction cup, and an analyte testing method. The reaction cup can allow the membrane strip to stand upright therein, and can be opened for operation, thereby reducing the area occupied by the reaction cup on the molecular hybridization instrument, and reducing the area of the molecular hybridization instrument. A plurality of reaction cups can be placed on the molecular hybridization instrument at the same time, which increases the number of tests and improves the utilization and working efficiency of the molecular hybridization instrument.

14 Claims, 10 Drawing Sheets

(52) U.S. Cl.
CPC ..... *B01L 2200/025* (2013.01); *B01L 2200/16* (2013.01); *B01L 2300/0825* (2013.01)

(56) References Cited

FOREIGN PATENT DOCUMENTS

| | | |
|---|---|---|
| CN | 102134552 A | 7/2011 |
| CN | 201933095 U | 8/2011 |
| CN | 201933096 U | 8/2011 |
| CN | 102707044 A | 10/2012 |
| CN | 203495980 U | 3/2014 |
| CN | 102115712 B | 5/2015 |
| CN | 205628758 U | 10/2016 |
| CN | 107014989 A | 8/2017 |
| CN | 107586701 A | 1/2018 |
| CN | 111254044 A | 6/2020 |
| JP | 2010091448 A | 4/2010 |
| WO | 2012066499 A1 | 5/2012 |
| WO | 2020108582 A1 | 6/2020 |

OTHER PUBLICATIONS

International Preliminary Report on Patentability issued in PCT/CN2019/121746 dated May 25, 2021—incl Engl lang transl.
Extended European Search Report issued in EP 19 89 0642 dated Jul. 29, 2022 (8 pages).

REACTION VESSEL, MOLECULAR HYBRIDIZATION APPARATUS, APPLICATION THEREOF, AND DETECTION METHOD

CROSS-REFERENCE TO RELATED MATTERS

The present invention is filed under 35 U.S.C. § 371 as the U.S. national phase of International Patent Application No. PCT/CN2019/121746, filed Nov. 28, 2019, which designated the United States and claims priority to Chinese Patent Application No. 201811460594.9, filed Dec. 1, 2018, each of which is hereby incorporated in its entirety including all tables, figures and claims.

FIELD OF THE INVENTION

The present invention relates to the field of molecular hybridization technology, and specifically relates to a reaction cup which can be applied to a molecular hybridization instrument, a molecular hybridization instrument using the reaction cup, and a testing method.

BACKGROUND OF THE INVENTION

Nucleic acid molecular hybridization is one of the most basic methods of gene diagnosis. Its basic principle is: complementary DNA single strands can be bound into a double strand under certain conditions, that is, can be hybridized. This binding is specific, that is, in strict accordance with the principle of base complementation, and it can be implemented not only between DNA and DNA, but also between DNA and RNA. Therefore, when a nucleotide sequence of a known gene as a probe is in contact with a denatured single-stranded genomic DNA, if the bases of the two are completely paired, they will be bound into a double strand in a complementary manner, which indicates that the tested genomic DNA containing the known gene sequence.

The working process of a full-automatic nucleic acid molecular hybridization instrument is to simulate the manual operation mode of the entire hybridization reaction, needs to complete multiple steps of addition of reagents, heat preservation, shaking, color development, and the like, connects reaction steps according to the hybridization reaction process to automatically complete an analysis item according to a preset program, finally analyzes the color development of a membrane strip, determines from the test result whether a specific DNA is contained, and thus determines whether a tested person is infected with a virus or carries a specific gene.

Most of the full-automatic nucleic acid molecular hybridization instruments in current market carry out reaction by placing a membrane strip in a horizontal recess, that is, the membrane strip is horizontally placed in the horizontal recess. On the one hand, because the liquid level in the horizontal reaction tank is closer to the opening, the moving liquid will spill from the tank during reciprocating motion of the reaction tank for mixing. Therefore, a cover has to be added to the tank to ensure that the liquid in the tank will not spill. However, the addition of the cover increases the complexity of operation when the membrane strip is placed and fetched. If the cover is closed tightly, the liquid in the reaction cup will still spill, which increases the risk of contamination of the reaction system. On the other hand, because the horizontal reaction tank uses a linear reciprocating mechanism, its design complexity and cost are high, and the reliability of mechanism motion is poor.

SUMMARY OF THE INVENTION

Aiming at the deficiencies of the prior art, the present invention provides a new reaction cup, in which a membrane strip can be placed upright and open operation can be achieved, so that the area of the reaction cup on a molecular hybridization instrument is reduced, and a plurality of reaction cups can be placed on the molecular hybridization instrument at the same time. The objective of the present invention is to provide a reaction cup, including cup walls and a cup bottom, wherein the cup walls are provided with clamping portions, the clamping portions can allow a membrane strip to stand upright in the reaction cup, and the connecting area of the two opposite clamping portions forms an upright placement position for the membrane strip.

The reaction cup can allow the membrane strip to stand upright therein, which greatly reduces the area occupied by the reaction cup on a molecular hybridization instrument, so that a plurality of reaction cups can be placed on the molecular hybridization instrument at the same time. In addition, the open reaction cup is convenient to operate.

Further, the clamping portion includes two adjacent cup walls and a junction of the two cup walls.

Further, the reaction cup includes first membrane strip upright positions and second membrane strip upright positions, and the distance between the first membrane strip upright positions is smaller than the distance between the second membrane strip upright positions. Further, a stop bar is mounted at a non-two-sides edge of the cup wall of the reaction cup, and the cup wall and the stop bar form a first clamping portion.

Further, the cup bottom of the reaction cup is provided with bosses corresponding to the clamping portions, and the membrane strip is placed on the bosses.

Further, the cup bottom is an inclined surface, and a recess is formed at a low position of the inclined surface.

In another aspect, the present invention further provides a nucleic acid molecular hybridization instrument, including an injection needle, an aspirating needle, a lifting mechanism, an injection pump, reagent bottles, a reaction disc provided with a cup trough, and the reaction cup of the present invention, wherein the cup trough is used to store the reaction cup.

Further, the reaction disc rotates under the drive of a motion mechanism.

Further, the present invention further involves an application of the reaction cup in nucleic acid analysis.

In another aspect, the present invention further provides a method for testing an analyte, including: (1) providing a membrane strip on which a test reagent is pre-fixed; (2) providing the reaction cup of the present invention; (3) placing the membrane strip in (1) upright in the reaction cup; (4) sequentially adding a sample and other reaction reagents to the reaction cup; and (5) after the reaction ends, taking the membrane strip out, and analyzing the test result according to the signal on the membrane strip.

Further, the test reagent pre-fixed on the membrane strip is a specific probe.

The beneficial effects of the present invention include: using the reaction cup of the present invention, the membrane strip can be placed upright in the reaction cup. (1) The upright placement of the membrane strip is beneficial to saving the whole space, and more test strips can be placed within the same projection area, which effectively saves the desktop space. (2) The membrane strip can be thoroughly cleaned, and the color development result is prevented from being affected by background color due to incomplete cleaning. (3) The membrane strip is kept upright at the clamping portions of the reaction cup, so that the membrane strip can be kept immobile during cleaning, and the membrane strip can be prevented from being damaged by laying the aspirating needle. (4) The reaction cup may also include multiple sizes of membrane strip upright positions, so that multiple kinds of membrane strips can be placed in the same cup to meet the requirements of different membrane strip sizes. (5) The upright square cup with clamping portions in the present invention facilitates the mixing of liquid in the reaction cup during rotation. (6) Because the analysis instrument has few restrictions in the upright direction, the reaction cup of the present invention can be designed to be high enough. The reaction cup with enough height can be open during use, which avoids the risk of spilling of the reaction liquid during mixing, ensures smooth reaction on the membrane strip in the open reaction system, and avoids many inconveniences caused by sealed reaction tank design in the operation process. (7) When the membrane strip can be placed upright in the reaction cup, the reaction disc of the molecular hybridization instrument for placing the reaction cup can be rotated for mixing. This rotation mixing method greatly reduces the design complexity and cost of the entire mechanism, and makes the full-automatic nucleic acid molecular hybridization instrument simpler in design structure, higher in reliability, smaller in size and lower in cost.

DETAILED DESCRIPTION OF EMBODIMENTS

The following embodiments further describe the present invention. These embodiments are not used to limit the scope of the present invention, but to provide a further understanding of the present invention.

Figure 4:
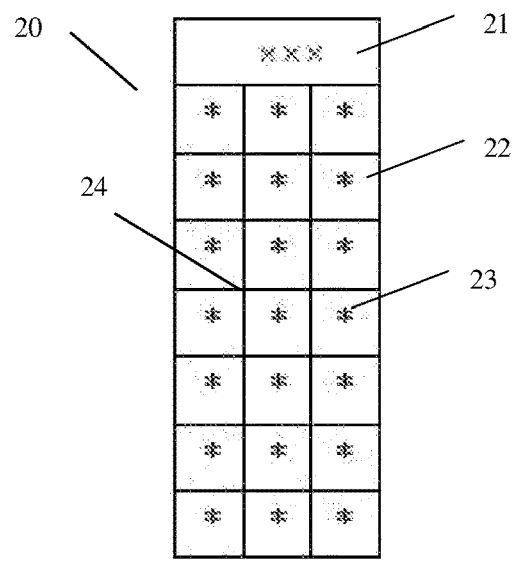
FIG. 4 is a schematic diagram of a membrane strip.

In the embodiment shown in FIG. 4, the shape of a membrane strip 20 is a rectangular thin paper sheet, and the material of the membrane strip is a nylon membrane having a thickness less than 1 mm. The thickness and size of the membrane strip can be adjusted according to the actual test requirements. The blank at a top 21 of the membrane strip is printed with a genotype item tested by the membrane strip and a number of the membrane strip, and a membrane surface 24 of the membrane strip is preset with an analysis reagent. In this embodiment, the membrane surface is divided into a plurality of small block areas 22, and each block is preset with a type of specific probe 23. After a series of reaction processes between a sample and the membrane strip, such as hybridization, membrane washing and color development, if the sample has an analyte corresponding to the probe in a certain area, the analyte will be bound with the specific probe on the area of the membrane strip, and the specific probe area on the membrane strip will develop a blue dot. A genotype corresponding to the sample can be identified based on the position of the color dot. In a specific embodiment, the membrane strip is applied to nucleic acid molecular detection, such as DNA or RNA detection. When DNA is detected, DNA or RNA can be used as a probe. When RNA is detected, DNA or RNA can be used as a probe.

Figure 1:
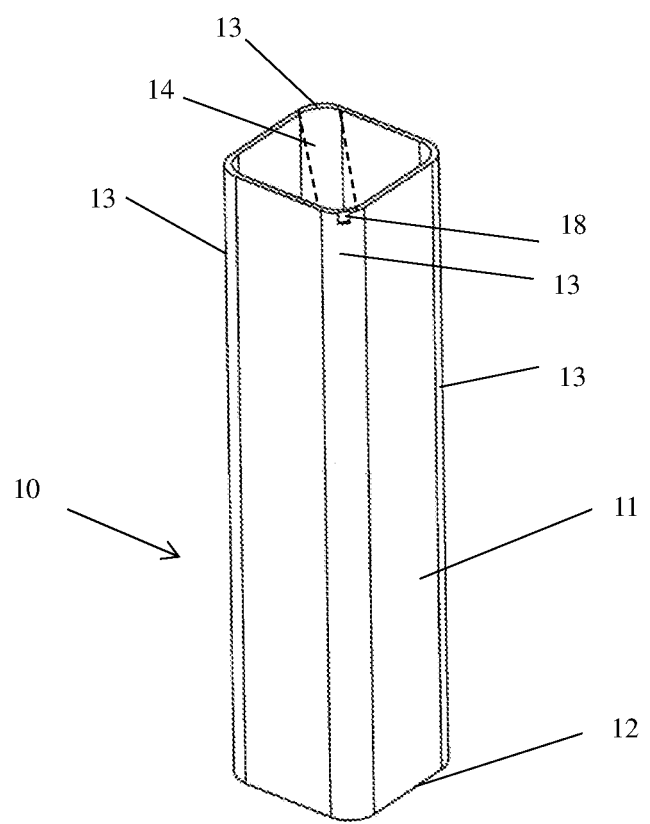
FIG. 1 is a schematic diagram of a reaction cup of the present invention (the dotted lines show upright placement positions of a membrane strip)
Figure 2:
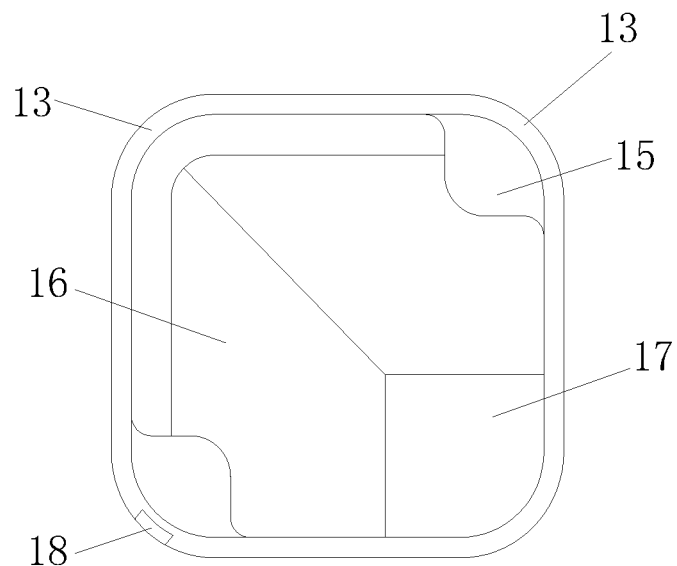
FIG. 2 is a top view of the reaction cup of the present invention.
Figure 3:
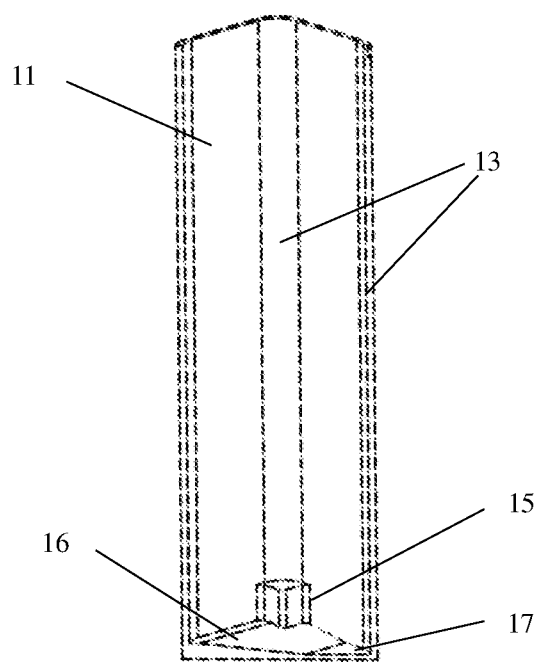
FIG. 3 is a cross-sectional view of the reaction cup of the present invention.

FIGS. 1-3 show a reaction cup 10 that can allow a membrane strip to stand upright therein, the reaction cup includes cup walls 11 and a cup bottom 12, and the cup walls are provided with clamping portions 13 that allow the membrane strip to stand upright in the reaction cup. In the upright square cup 10 shown in FIGS. 1-3, a clamping portion 13 includes two adjacent cup walls and a junction (cup corner) of the two cup walls, the connecting area of two opposite cup corners form a membrane strip upright position 14 (as shown by dotted lines in FIG. 1), and the width of the membrane strip upright position can allow the membrane strip to be placed therein smoothly and kept upright (the width refers to the distance between two opposite cup corners).

Figure 5:
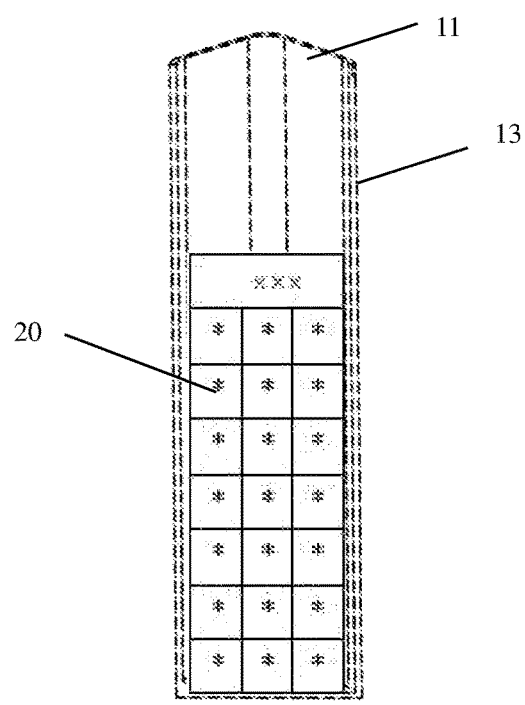
FIG. 5 is a cross-sectional view of the membrane strip placed upright in the reaction cup.

As shown in FIG. 5, the membrane strip 20 is placed upright in the reaction cup 10, two sides of the membrane strip 20 are respectively placed at the diagonal clamping portions 13, and the membrane strip 20 is blocked by the cup walls 11 and does not greatly rotate in the reaction cup 10, thereby ensuring that the membrane strip 20 is substantially retained at the membrane strip upright position 14 after a series of reaction processes such as hybridization, membrane washing and color development, and preventing the membrane strip 20 from greatly rotating, and even from rotating to a laying position of an aspirating needle 4 to cause the aspirating needle 4 to touch and pierce the membrane strip when being laid.

The reaction cup 10 of the present invention can ensure that the membrane strip is placed upright in the reaction cup, so compared with the situation that the membrane strip is horizontally placed in the reaction cup, the area occupied by the former membrane strip is much smaller than the area occupied by the latter membrane strip. Thus, in the same area, a molecular hybridization instrument using the reaction cup of the present invention can carry more membrane strips simultaneously.

The membrane strip 20 placed in the reaction cup 10 needs to fully contact the reagent to complete the processes of membrane strip cleaning and the like, and is also prevented from contacting the aspirating needle. In the present invention, the clamping portions 13 on the reaction cup restrict the movement space of the membrane strip 20, so that the membrane strip 20 cannot be greatly moved in the reaction cup, but can be in full contact with the reagent.

Figure 13:
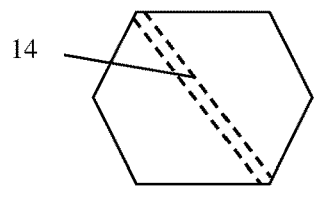
FIG. 13 is a schematic cross-sectional view of another reaction cup and membrane strip upright position of the present invention.
Figure 14:
FIG. 14 is a schematic cross-sectional view of another reaction cup of the present invention and clamping portions thereof.
Figure 15:
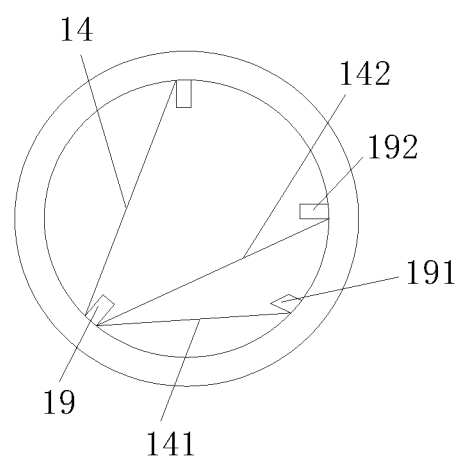
FIG. 15 is a schematic cross-sectional view of a round reaction cup and membrane strip upright position of the present invention.

The cup walls are provided with clamping portions 13 that allow the membrane strip to stand upright in the reaction cup. In the embodiment shown in FIGS. 1-3, 7, 8, 11, 12 and 13, a clamping portion 13 includes two adjacent cup walls and a junction of the two cup walls. In the embodiment shown in FIG. 9, the clamping portion 13 includes a cup wall and a stop bar, and a junction of the cup wall and the stop bar. Specifically, a stop bar 19 is mounted on the cup wall 11 of the reaction cup, the cup wall 11 and the stop bar 19 form a first clamping portion 13, a second clamping portion 132 opposite to the first clamping portion 131 is formed by two adjacent cup walls 11 and a junction thereof, and a first membrane strip upright position 141 is formed between the first clamping portion 131 and the second clamping portion 132. In the embodiment shown in FIG. 10, stop bars 19 are arranged at cup corners, clamping grooves 191 are formed at middle parts of the stop bars 19, two sides of the membrane strip are respectively inserted into the clamping grooves 191, and the clamping grooves 191 are clamping portions. In the embodiment shown in FIG. 14, the inner wall of the reaction cup is provided with a sawtooth structure, and the clamping portions 13 are gaps between sawteeth. In the embodiment shown in FIG. 15, the reaction cup is a circular cup, stop bars 19, 191 and 192 are arranged at different positions of the inner wall of the circular cup, clamping portions are formed between the stop bars and the inner wall of the circular cup, and membrane strip upright positions 14, 141 and 142 are formed between the opposite clamping portions. The stop bars are arranged at different positions of the inner wall to form the membrane strip upright positions with different widths. In the examples of FIGS. 14 and 15, membrane strips with different widths can be simultaneously placed in a reaction cup.

Figure 7:
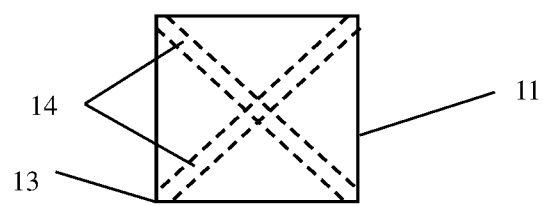
FIG. 7 is a schematic cross-sectional view of a reaction cup and membrane strip upright position of the present invention.
Figure 8:
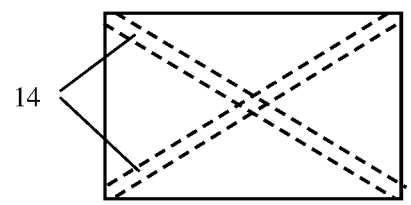
FIG. 8 is a schematic cross-sectional view of another reaction cup and membrane strip upright position of the present invention.
Figure 11:
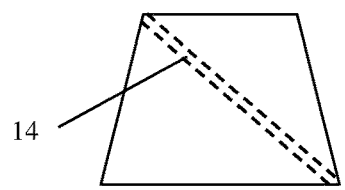
FIG. 11 is a schematic cross-sectional view of another reaction cup and membrane strip upright position of the present invention.
Figure 12:
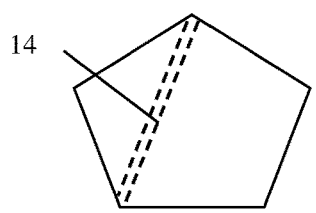
FIG. 12 is a schematic cross-sectional view of another reaction cup and membrane strip upright position of the present invention.

As shown in FIGS. 1, 7 and 8, the cross section of the reaction cup 10 is of an approximately square structure, a square structure or a rectangular structure, two membrane strip upright positions 14 are respectively formed between the two opposite clamping portions 13, and the two membrane strip upright positions have the same size and can be used for placing membrane strips 20 with the same size. The cross section of the reaction cup shown in FIGS. 11, 12 and 13 is polygons such as trapezoidal, pentagonal, hexagonal or parallelogram, and membrane strip upright positions are formed between the two opposite clamping portions in the reaction cup.

In order to place membrane strips 20 with different sizes in the same reaction cup 10, it can be achieved by changing the shape of the reaction cup 10 in some embodiments. For example, the cross section of the reaction cup is of an irregular quadrangle, resulting in different lengths of connecting lines between spaced (opposite) clamping portions, that is, forming membrane strip upright positions with different sizes. For example, the cross section of the reaction cup is of an irregular pentagon, an irregular hexagon, and the like.

Figure 9:
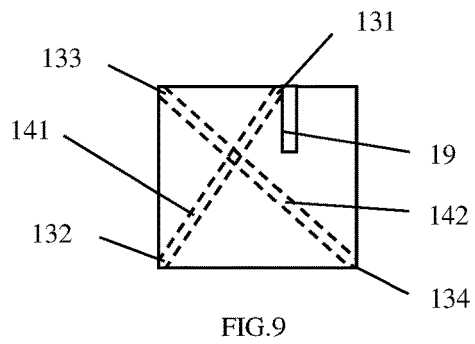
FIG. 9 is a schematic cross-sectional view of the reaction cup in FIG. 5 with a third membrane strip upright position formed with a stop bar.

In some other embodiments, stop bars 19 are arranged on the cup walls of the reaction cup 10 to form membrane strip upright positions with different sizes. As shown in FIG. 9, a stop bar 19 is mounted on the inner side of a cup wall 11 of the square reaction cup 10, the cup wall 11 and the stop bar 19 form a first clamping portion 131, a second clamping portion 132 opposite to the first clamping portion 131 is formed by two adjacent cup walls 11 and a junction thereof, and a first membrane strip upright position 141 is formed between the first clamping portion 131 and the second clamping portion 132; and a second membrane strip upright position 142 is formed between a third clamping portion 133 and a fourth clamping portion 134 adjacent to the second clamping portion. By arranging the stop bar, the first membrane strip upright position is narrower than the second membrane strip upright position, so that membrane strips with different widths can be placed in a reaction cup to meet the requirement that the reaction cup can be applied to different membrane strip sizes. The narrower membrane strip is placed at the first membrane strip upright position 141, and the wider membrane strip is placed at the second membrane strip upright position 142. In this embodiment, the stop bar is perpendicular to the cup wall. In other embodiments, the stop bar is not perpendicular to the cup wall. In this embodiment, the stop bar 19 is as long as the membrane strip. In other embodiments, the stop bar 19 may have other suitable length, as long as the membrane strip can be stably located in the clamping portion.

Figure 10:
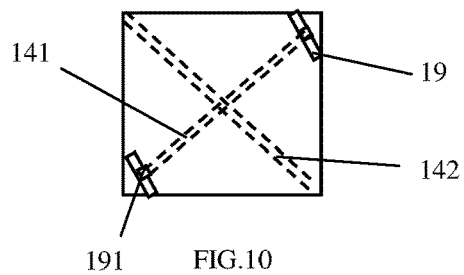
FIG. 10 is a schematic cross-sectional view of the reaction cup in FIG. 5 with another third membrane strip upright position formed with a stop bar.

As shown in FIG. 10, a stop bar 19 is respectively arranged at a pair of opposite corners of the reaction cup, a clamping groove 191 is formed at a middle part of the stop bar 19, two sides of the membrane strip are respectively inserted into the clamping grooves 191, the clamping grooves 191 are clamping portions, first membrane strip upright positions 141 are formed between two opposite clamping grooves, and second membrane strip upright positions 142 are formed between the other two corners (clamping portions). The distance between the first membrane strip upright positions is smaller than the distance between the second membrane strip upright positions, so that multiple kinds of membrane strips can be placed in a reaction cup to meet the requirements of different membrane strip sizes. Narrower membrane strips are placed at the first membrane strip upright positions, and wider membrane strips are placed at the second membrane strip upright positions.

The reaction cup 10 may be an upright square cup, round mug, or the like. The reaction cup is placed on a reaction disc 1 of the hybridization instrument, the reaction disc 1 is rotated back and forth to drive thorough mixing of the reagent in the reaction cup, and the reagent is in full contact with the membrane strip to ensure smooth reaction. When the reaction disc is rotated back and forth, the upright reaction cup 10 is more beneficial to the mixing of the liquid in the reaction cup. When the reaction cup is a square cup, the shape of the square cup is different from the reciprocating trajectory of liquid, and the reciprocating liquid easily hits the cup walls, so that the liquid can be mixed more thoroughly. When the reaction cup is a round cup, the circular cup wall is similar or close to the reciprocating trajectory of liquid, so the liquid is unlikely to hit the cup wall, and the degree of mixing is lower than that in the square cup.

In order to smoothly suck the reaction liquid in the reaction cup by the aspirating needle, or to facilitate liquid flow in the reaction cup, in a preferred scheme, the cup bottom 12 of the reaction cup 10 further includes bosses 15, the bosses are correspondingly formed at the clamping portions, the bosses 15 are arranged at bottoms of the membrane strip upright positions, the membrane strip 20 put into the reaction cup 10 is placed on the bosses 15, and a certain gap is retained between the membrane strip 20 and the cup bottom 12, which facilitates the flowing of the sucked liquid or the reaction reagent in the reaction cup 10.

In another preferred scheme, the cup bottom 12 is an inclined surface 16, a recess 17 is formed at a low position of the inclined surface 16, and the liquid flowing down from the inclined surface 16 can be accumulated in the recess 17. During liquid suction, the recess 17 in the reaction cup is just below the aspirating needle 4 of the molecular hybridization instrument. A small amount of residual liquid that needs to be removed in the reaction cup 10 will flow down along the inclined surface 16 and converge in the recess 17, which is more advantageous for the aspirating needle to suck the residual liquid away. In this embodiment, the recess 17 is formed at a corner of the bottom 12 of the reaction cup.

In order to ensure that the membrane strip is placed in the reaction cup in a correct direction, a fool-proof member is arranged on the reaction cup, for example, a membrane strip placing direction indication 18 is arranged on the outer wall of the rim of the reaction cup shown in FIG. 1, and two sides of the membrane strip are inserted into the reaction cup from the indication. The indication 18 is the fool-proof member. The fool-proof member may also be in other forms, for example, but not limited to, line indication, bump indication, and the like.

Figure 16:
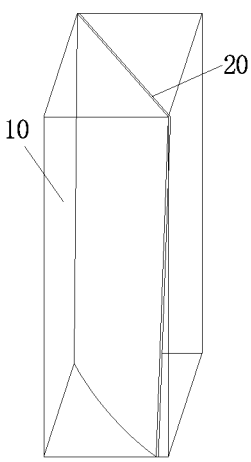
FIG. 16 is a schematic diagram showing a certain angle of the membrane strip and the bottom of the reaction cup.
Figure 17:
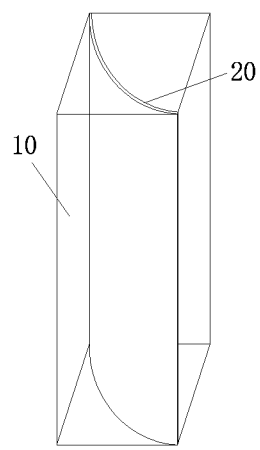
FIG. 17 is a schematic diagram showing a certain radian of the membrane strip.

In the present invention, the membrane strip being upright in the reaction cup refers to that the membrane surface of the membrane strip is not parallel to the bottom surface of the reaction cup, but is at a certain angle with the bottom surface of the cup, including but not limited to the following states. As shown in FIG. 5, the membrane strip is upright in the reaction cup, and the membrane surface is perpendicular to the bottom surface of the cup. As shown in FIG. 16, the membrane surface of the membrane strip is at a certain angle with the bottom surface of the cup, for example, a 30-degree angle. As shown in FIG. 17, after the membrane strip is placed in the reaction cup, the membrane surface exhibits a certain bending.

A method for testing an analyte by hybridization includes: (1) providing a membrane strip on which a test reagent is pre-fixed; (2) providing the reaction cup of the present invention; (3) placing the membrane strip in (1) upright in the reaction cup of the present invention; (4) sequentially adding a sample and other reaction reagents to the reaction cup; and (5) after the reaction ends, taking the membrane strip out, and analyzing the test result according to the signal on the membrane strip.

In a specific embodiment of testing an analyte by nucleic acid molecular hybridization, the method includes: (1) providing a membrane strip on which a specific probe is pre-fixed; (2) providing the reaction cup of the present invention; (3) placing the membrane strip in (1) upright in the reaction cup of the present invention; (4) sequentially adding a sample and other reaction reagents to the reaction cup; and (5) after the reaction ends, taking the membrane strip out, and analyzing the test result according to the signal on the membrane strip.

Figure 21:
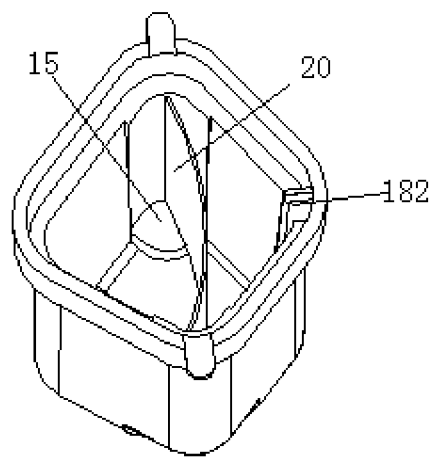
FIG. 21 is a schematic diagram showing that the membrane strip is placed into the reaction cup.

As shown in FIGS. 18 to 21, a suction zone 17 holding an aspirating needle is formed at the inner bottom of the cup. In a preferred design scheme, the suction zone is a recess structure. Specifically, the cup bottom is an inclined surface, a recess 17 is formed at a low position of the inclined surface, and liquid at the bottom of the cup flows down along the inclined surface and converges in the recess 17. In this embodiment, the recess 17 is formed at a corner of the bottom of the reaction cup, lugs 181 are arranged at the rim of the cup, and the projections of the lugs 181 at the bottom of the cup are located on two sides of the corner where the recess is located. As shown in FIG. 21, the lugs are used to remind the operator to place the membrane strip 20 upright along the diagonal of the two lugs 181. After the membrane strip is placed according to the indication of the lugs 181, the corresponding position of the recess 17 will not be blocked by the membrane strip, which ensures that the sampling needle does not touch the membrane strip to damage the membrane strip when entering the reaction cup to suck liquid each time.

Another structure for confirming the placement position of the membrane strip is a flange 182 formed in the reaction cup, and the flange is at a diagonal position of the recess 17 and protrudes into the reaction cup. As shown in FIG. 21, when the operator places the membrane strip in the diagonal direction of the recess 17 and the flange 182 by mistake, because of the blocking of the flange, the membrane strip cannot be placed down in the reaction cup. This reminds the operator that the membrane strip is placed in a wrong direction and needs to be reset, thereby ensuring that the corresponding position of the recess 17 will not be locked by the membrane strip. In a preferred scheme, the flange 182 is arranged at the opening of the reaction cup and can extend to the bottom of the cup.

Generally, the position of the aspirating needle on the hybridization instrument is fixed, while the reaction cup is placed in the hybridization instrument from the outside by manual operation or a mechanical arm. This requires the suction zone of the reaction cup placed in the hybridization instrument at a correct suction position of the sampling needle. In the embodiment shown in FIG. 19, the cross section of the opening of the reaction cup is designed into an isosceles trapezoid, and the trapezoid is identical to the shape of a cup trough opening of the reaction disc 1 of the hybridization instrument (the cup trough opening of the hybridization instrument is not shown). When the reaction cup is placed in a way that the long edge of the opening of the reaction cup is opposite to the short edge of the cup trough opening, the reaction cup cannot be placed in a cup trough, thereby ensuring that the suction zone of the reaction cup placed in the hybridization instrument is at the correct suction position of the sampling needle. Based on such design idea, the cross section of the opening of the reaction cup and the cup trough opening can be designed into other suitable shapes, such as non-isosceles trapezoids.

Figure 18:
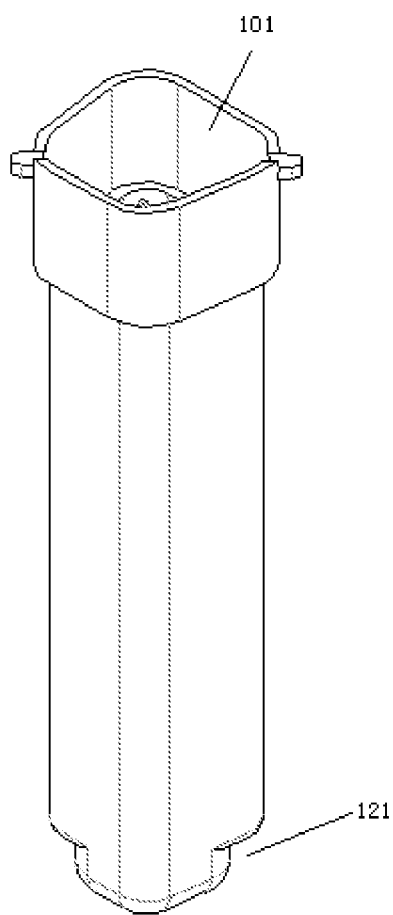
FIG. 18 is a schematic diagram of another reaction cup of the present invention.
Figure 19:
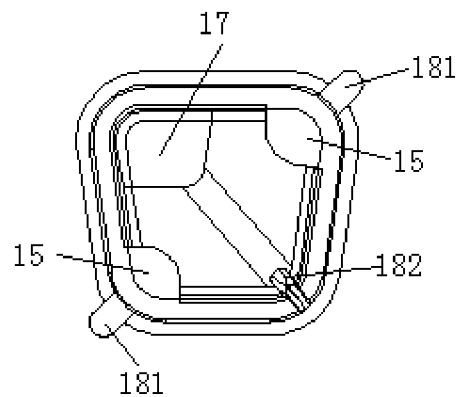
FIG. 19 is a top view of FIG. 18, showing the internal structure of the reaction cup.
Figure 20:
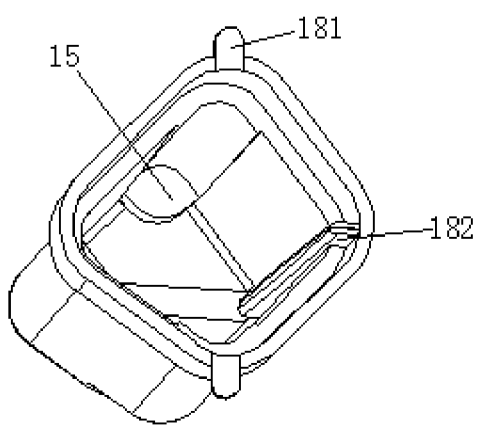
FIG. 20 is a schematic diagram showing an inclination angle of the reaction cup shown in FIG. 18.
Figure 22:
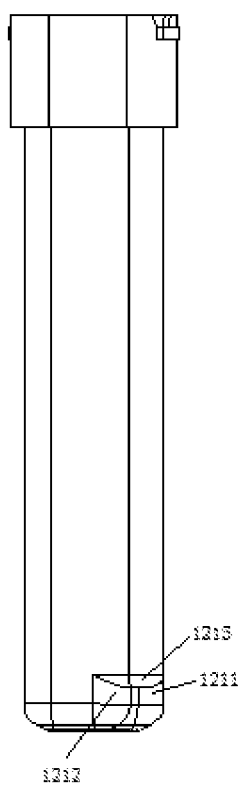
FIG. 22 is a schematic diagram of a reaction cup with a recessed area at the bottom.
Figure 23:
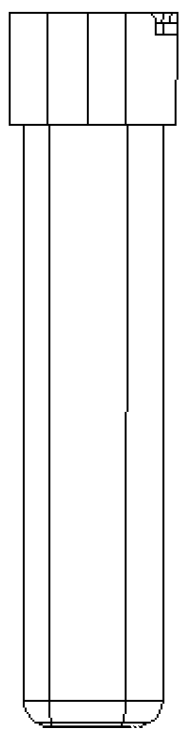
FIG. 23 is a schematic diagram of a reaction cup with a conventional bottom.

The cup bottom of the reaction cup shown in FIGS. 18 and 22 is recessed. For example, side walls of cup bottom corners of the reaction cup are closer to the center of the reaction cup than side walls of the cup body, bottoms of the cup bottom corners of the reaction cup are closer to the opening of the cup than the cup bottom, then a recessed area 121 is formed, and three cup walls 1211, 1212 and 1213 are respectively in this area. Thus, the reaction cup shown in FIGS. 18 and 22 has larger cup wall area than the cup shown in FIG. 23. As the cup wall area increases, the area of contact between the cup walls and a heat source also increases, which increases the speed of heating the reaction cup by the hybridization instrument.

Figure 6:
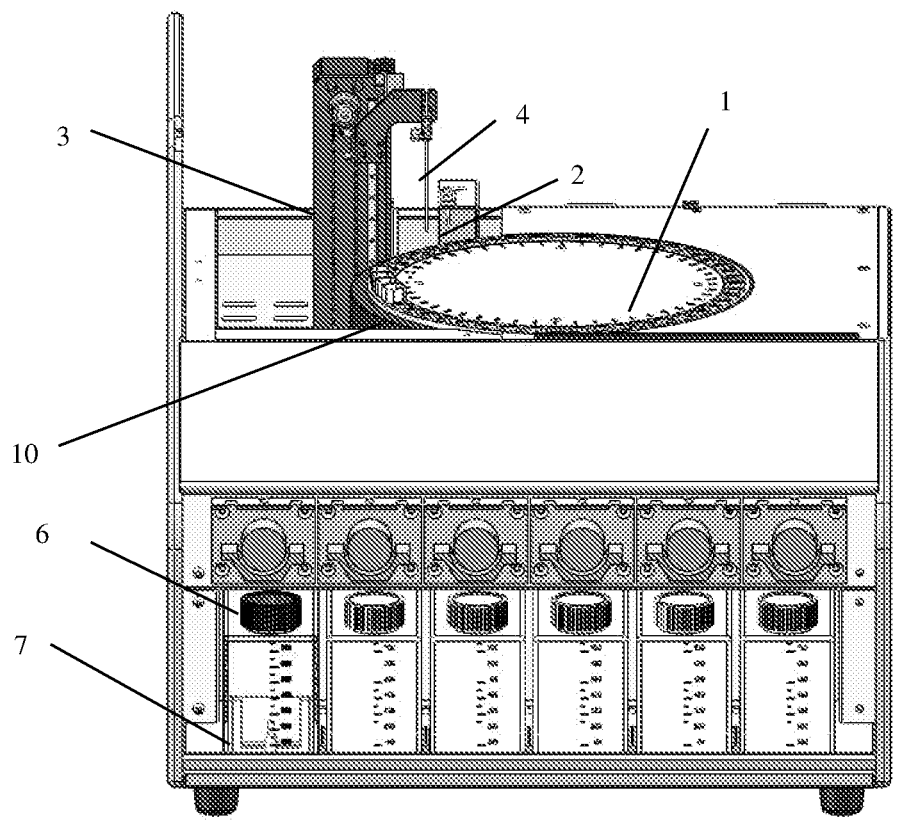
FIG. 6 is a schematic diagram of a molecular hybridization instrument of the present invention.

Embodiment 1 Application of the Reaction Cup 10 of the Present Invention in a Full-Automatic Nucleic Acid Molecular Hybridization Instrument As shown in FIG. 6, the full-automatic nucleic acid molecular hybridization instrument mainly includes: a reaction disc 1, an injection needle 2, a lifting mechanism 3, an aspirating needle 4, an injection pump 6, and reagent bottles 7.

The working process of the full-automatic nucleic acid molecular hybridization instrument is described as follows:

1. The reaction cup 10 in which the membrane strip 20 is placed is placed in a cup trough on the reaction disc 1. In this embodiment, 48 reaction cups 10 can be placed in the instrument.
2. The instrument uses the injection pump 6 to inject a solution I in the reagent bottle 7 to the reaction cup 10 via the injection needle 2.
3. After the solution I is injected into the reaction cup 10, a sample to be analyzed is sequentially injected into each reaction cup 10, and after the sample is injected, a hybridization process is activated (about 30 min).
4. During hybridization, the reaction disc 1 is rotated back and forth to drive thorough mixing of the liquid in the reaction cups to ensure smooth reaction.
5. After the hybridization process ends, the reaction cups are sequentially rotated to be under the aspirating needle 4, the lifting mechanism 3 lowers the aspirating needle to the bottom of the reaction cup, and then a waste liquid pump sucks away the residual reaction liquid in the cup.
6. The reaction cups are then sequentially rotated to be under the injection needle 2, and the injection pump 6 injects a solution II in the reagent bottle 7 into the reaction cups 10 via the injection needle 2.
7. After the solution II is injected, a membrane washing process is activated (about 10 min). During washing, the reaction disc 1 is rotated back and forth to drive thorough mixing of the liquid in the reaction cups to ensure smooth reaction.
8. After the membrane washing process ends, the reaction cups are sequentially rotated to be under the aspirating needle 4, the lifting mechanism 3 lowers the aspirating needle to the bottom of the reaction cup, and then the waste liquid pump sucks away the residual reaction liquid in the cup.
9. The reaction cups 10 are sequentially rotated to be under the injection needle 2 again, and the injection pump 6 injects a binding liquid in the reagent bottle 7 into the reaction cups via the injection needle 2.
10. After the binding liquid is injected, a binding process is activated (about 10 min). During the catalytic process, the reaction disc 1 is rotated back and forth to drive thorough mixing of the liquid in the reaction cups to ensure smooth reaction.
11. After the binding process ends, the reaction cups are sequentially rotated to be under the aspirating needle 4, the lifting mechanism 3 lowers the aspirating needle to the bottom of the reaction cup, and then the waste liquid pump sucks away the residual reaction liquid in the cup.
12. The reaction cups are sequentially rotated to be under the injection needle again, and the injection pump 6 injects the solution I in the reagent bottle 7 into the reaction cups via the injection needle 2.
13. After the solution I is injected, a first cleaning process is activated (about 10 min). During cleaning, the reaction disc 1 is rotated back and forth to drive thorough mixing of the liquid in the reaction cups to ensure smooth reaction.
14. After the cleaning process ends, the reaction cups are sequentially rotated to be under the aspirating needle 4, the lifting mechanism 3 lowers the aspirating needle to the bottom of the reaction cup, and then the waste liquid pump sucks away the residual reaction liquid in the cup.
15. The reaction cups are sequentially rotated to be under the injection needle again, and the injection pump 6 injects the solution III in the reagent bottle 7 into the reaction cups via the injection needle 2.
16. After the solution III is injected, a second cleaning process is activated (about 3 min). During cleaning, the reaction disc 1 is rotated back and forth to drive thorough mixing of the liquid in the reaction cups to ensure smooth reaction.
19. After the cleaning process ends, the reaction cups are sequentially rotated to be under the aspirating needle 4, the lifting mechanism 3 lowers the aspirating needle to the bottom of the reaction cup, and then the waste liquid pump sucks away the residual reaction liquid in the cup.
20. The reaction cups are sequentially rotated to be under the injection needle again, and the injection pump 6 injects a color development liquid in the reagent bottle 7 into the reaction cups via the injection needle 2.
21. After the color development liquid is injected, a color development process is activated (about 10 min). During the color development process, the reaction disc 1 is rotated back and forth to drive thorough mixing of the liquid in the reaction cups to ensure smooth reaction.
22. After the color development process ends, the reaction cups are sequentially rotated to be under the aspirating needle 4, the lifting mechanism 3 lowers the aspirating needle to the bottom of the reaction cup, and then the waste liquid pump sucks away the residual reaction liquid in the cup.
23. The reaction cups are sequentially rotated to be under the injection needle again, and the injection pump 6 injects purified water in the reagent bottle 7 into the reaction cups via the injection needle 2.
24. After the purified water is injected, a color development termination process is activated (about 3 min). During the color development termination process, the reaction disc 1 is rotated back and forth to drive thorough mixing of the liquid in the reaction cups to ensure smooth reaction.

25. After the color development termination process ends, the reaction cups 10 are sequentially rotated to be under the aspirating needle 4, the lifting mechanism 3 lowers the aspirating needle to the bottom of the reaction cup, and then the waste liquid pump sucks away the residual reaction liquid in the cup.

26. After the purified water in the reaction cups 10 is completely sucked, the membrane strips 20 in the reaction cups are sequentially taken out, and the test results are read from the color development positions on the membrane strips 20.

The solution includes:
Solution I: 10% 20*SSC, 1% SDS
Solution II: 2.5% 20*SSC, 1% SDS
Solution III: 0.1M sodium citrate
Binding liquid: POD: solution I=1:30000
Color development liquid: 2 mg/ml TMB: 30% H2O2: Solution III=500:1:9500
Among them:
20*SSC: 175 g NaCl, 88.2 g sodium citrate, add 800 ml of pure water for dissolving, regulate the pH value to 7.0 with concentrated HCl, fix the volume to 1000 ml, and high pressure sterilization. Preserve at normal temperature.
10% SDS: dissolve 20 g SDS in 180 ml of purified water, regulate the pH value to 7.0 with 1M HCl, and fix the volume to 200 ml. Preserve at normal temperature.
1M sodium citrate: dissolve 294.1 g sodium citrate in 700 ml of purified water, regulate the pH value to 5.0 with concentrated HCl, and fix the volume to 1000 ml. Preserve at normal temperature.
POD: avidin-coupled catalase Embodiment 2 Use a Reverse Dot Blotting Method to Test Human Papilloma Virus (HPV) Genotypes of Samples Membrane strips on which 14 kinds of high-risk HPV genotype specific probes are fixed are placed upright at the membrane strip upright positions of the reaction cups of the present invention. The 14 kinds of high-risk genotypes: HPV16, 18, 31, 33, 35, 39, 45, 51, 52, 56, 58, 59, 68, 73. The reaction cups in which the membrane strips are placed are placed in the cup troughs of the reaction disc of the full-automatic nucleic acid molecular hybridization instrument, the full-automatic nucleic acid molecular hybridization instrument are activated, and the working process of the hybridization instrument follows Embodiment 1. After the hybridization instrument finishes the working process described in Embodiment 1, the membrane strips are taken out, and whether the tested samples contain these HPV genotypes is detected according to the hybridization signals on the membrane strips. The test results show that the typing results obtained by hybridization when the membrane strips are placed upright in the reaction cups of the present invention are accurate. After the operation of the full-automatic nucleic acid molecular hybridization instrument ends, no solution spills out from the reaction cups due to the reciprocating movement of the instrument.

The invention claimed is:

1. A reaction cup, comprising
cup walls and a cup bottom, wherein the cup is configured and arranged to receive and hold a membrane strip in an upright position within the cup between two clamping portions comprised by the cup walls, wherein the cup comprises a boss at the base of at least one clamping portion configured and arranged such that a membrane strip received in the reaction cup rests on the at least one boss thereby creating a gap between the membrane strip and the cup bottom, and wherein the cup bottom comprises a recessed portion forming a low point within the cup bottom at a location distal to the at least one.

2. The reaction cup according to claim 1, wherein the cup bottom is an inclined surface, and the recessed portion of the cup bottom is formed at a low position of an inclined surface.

3. The reaction cup according to claim 1, wherein the clamping portion comprises two adjacent cup walls and a junction of the two adjacent cup walls.

4. The reaction cup according to claim 3, wherein the cup bottom is an inclined surface, and the recessed portion of the cup bottom is formed at a low position of the inclined surface.

5. The reaction cup according to claim 1, wherein the reaction cup comprises first membrane strip upright positions and second membrane strip upright positions, and a distance between the first membrane strip upright positions is smaller than the a distance between the second membrane strip upright positions.

6. The reaction cup according to claim 5, wherein the cup bottom is an inclined surface, and the recessed portion of the cup bottom is formed at a low position of the inclined surface.

7. A molecular hybridization instrument, comprising:
the reaction cup according to claim 1;
a reaction disc provided with a cup trough, wherein the reaction cup trough is used to store the reaction cup;
a plurality of reagent bottles situated below the reaction disc;
an injection needle above the reaction disc, for transferring solution from the plurality of reagent bottles to the reaction cup; and
an aspirating needle on a lifting mechanism above the reaction disc, for removing reaction liquid from the reaction cup.

8. The molecular hybridization instrument to claim 7 wherein the cup bottom is an inclined surface, and a recess is formed at a low position of the inclined surface.

9. The molecular hybridization instrument to claim 7, wherein the clamping portion comprises two adjacent cup walls and a junction of the two cup walls.

10. The molecular hybridization instrument to claim 9, wherein the cup bottom is an inclined surface, and the recessed portion of the cup bottom is formed at a low position of the inclined surface.

11. The molecular hybridization instrument to claim 7, wherein the reaction cup comprises first membrane strip upright positions and second membrane strip upright positions, and a distance between the first membrane strip upright positions is smaller than a distance between the second membrane strip upright positions.

12. The molecular hybridization instrument to claim 11, wherein the cup bottom is an inclined surface, and the recessed portion of the cup bottom is formed at a low position of the inclined surface.

13. A method for testing an analyte, comprising:
(1) providing a membrane strip on which a test reagent is pre-fixed;
(2) providing a reaction cup according to claim 1;
(3) placing the membrane strip in (1) upright in the reaction cup;
(4) sequentially adding a sample and other reaction reagents to the reaction cup; and (5) after the reaction ends, taking the membrane strip out, and analyzing the test result according to the signal on the membrane strip; wherein the reaction cup comprising cup walls and a cup bottom, wherein the cup walls are provided with clamping portions, the clamping portions can allow a membrane strip to stand upright in the reaction cup, and the connecting area of the two opposite clamping portions forms an upright placement position for the membrane strip.

14. The method according to claim 13, wherein the clamping portion comprises two adjacent cup walls and a junction of the two cup walls.

* * * * *